(12) United States Patent
Shah

(10) Patent No.: US 8,971,495 B2
(45) Date of Patent: Mar. 3, 2015

(54) METHOD AND APPARATUS FOR POWER CONTROL IN AN IMAGE-BASED NAVIGATION SYSTEM

(75) Inventor: Jigney Shah, Ashland, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 924 days.

(21) Appl. No.: 13/151,649

(22) Filed: Jun. 2, 2011

(65) Prior Publication Data

US 2012/0307971 A1 Dec. 6, 2012

(51) Int. Cl.
| | | |
|---|---|---|
| H05G 1/10 | (2006.01) | |
| A61B 6/03 | (2006.01) | |
| A61B 6/12 | (2006.01) | |
| A61B 6/00 | (2006.01) | |
| A61B 19/00 | (2006.01) | |
| A61B 17/00 | (2006.01) | |

(52) U.S. Cl.
CPC . *A61B 6/032* (2013.01); *A61B 6/12* (2013.01); *A61B 6/4405* (2013.01); *A61B 6/547* (2013.01); *A61B 6/56* (2013.01); *A61B 19/5244* (2013.01); *A61B 6/4441* (2013.01); *A61B 2017/00137* (2013.01); *A61B 2017/00734* (2013.01); *A61B 2019/4894* (2013.01); *A61B 2019/524* (2013.01); *A61B 2019/5251* (2013.01); *A61B 2019/5255* (2013.01); *A61B 6/508* (2013.01)
USPC ........................................ 378/103; 378/101

(58) Field of Classification Search
CPC ............................ A61B 6/4233; A61B 6/4405
USPC ................... 378/114, 101, 102, 103
See application file for complete search history.

(56) References Cited

U.S. PATENT DOCUMENTS

| | | | |
|---|---|---|---|
| 4,797,907 A | 1/1989 | Anderton | |
| 5,226,064 A | 7/1993 | Yahata et al. | |
| 5,592,939 A | 1/1997 | Martinelli | |
| 5,808,376 A | 9/1998 | Gordon et al. | |

(Continued)

FOREIGN PATENT DOCUMENTS

| | | |
|---|---|---|
| EP | 0946082 A1 | 9/1999 |
| WO | WO-2012166898 A1 | 12/2012 |

OTHER PUBLICATIONS

"Mayfield® Skull Clamps and Headrest Systems," Mayfield® Surgical Devices Product Index, pp. 1-6, Dec. 2004 Integra LifeSciences Corporation.

(Continued)

*Primary Examiner* — Hoon Song
(74) *Attorney, Agent, or Firm* — Harness, Dickey

(57) ABSTRACT

An imaging system can include an imaging capturing portion, an image processing unit, a main power supply and a supplemental power supply. The image capturing portion can include a source that emits an emission signal towards a target to be imaged, and a receiver that receives the emission signal emitted by the source. The image processing unit can receive the received emission signal from the imaging capturing portion and generate image data based on the received emission signal. The main power supply can be coupled to the imaging capturing portion and the imaging processing unit for providing operational power thereto. The supplemental power supply can be coupled to the main power supply and the imaging processing unit. The supplemental power supply can be charged by the main power supply in a first mode and provide operational power to the imaging processing unit in a second mode.

19 Claims, 4 Drawing Sheets

(56) References Cited

U.S. PATENT DOCUMENTS

| | | | |
|---|---|---|---|
| 5,867,561 A * | 2/1999 | Strasser et al. | 378/98.2 |
| 5,913,820 A | 6/1999 | Bladen et al. | |
| 5,983,126 A | 11/1999 | Wittkampf | |
| 6,298,116 B1 | 10/2001 | Methley et al. | |
| 6,474,341 B1 | 11/2002 | Hunter et al. | |
| 6,747,539 B1 | 6/2004 | Martinelli | |
| 6,940,941 B2 | 9/2005 | Gregerson et al. | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 7,751,865 B2 | 7/2010 | Jascob et al. | |
| 7,797,032 B2 | 9/2010 | Martinelli et al. | |
| 2004/0116803 A1 | 6/2004 | Jascob et al. | |
| 2004/0199072 A1 | 10/2004 | Sprouse et al. | |
| 2010/0220837 A1 | 9/2010 | Bressel | |
| 2010/0228117 A1 * | 9/2010 | Hartmann | 600/424 |
| 2011/0123001 A1 * | 5/2011 | Kopcienski et al. | 378/198 |

OTHER PUBLICATIONS

"Medtronic O-Arm Multi-Dimensional Surgical Imaging System"; Brochure, 24pp, 2009.

"StealthStation_S7_System® Information Center in the OR," (2009) Medtronic, Inc.

"StealthStation® TRIA™ plus Treatment Guidance System," brochure, Medtronic Surgical Navigation Technologies (2004) 2 pages.

"TREON, StealthStation," brochure, Medtronic Surgical Navigation Technologies (2001) 8 pages.

"AxiEM Electromagetic Navigation," tri-fold brochure, Medtronic Navigation (2005) 2 pages.

International Search Report and Written Opinion mailed Sep. 4, 2012 for PCT/US2012/040180 claiming benefit of U.S. Appl. No. 13/151,649, filed Jun. 2, 2011.

* cited by examiner

METHOD AND APPARATUS FOR POWER CONTROL IN AN IMAGE-BASED NAVIGATION SYSTEM

FIELD

The present disclosure is related to an image-based navigation system and, more particularly, to an image-based navigation system that includes advanced power management features to provide high-performance.

BACKGROUND

This section provides background information related to the present disclosure which is not necessarily prior art.

A subject, such as a human patient, may select or be required to undergo a surgical procedure to correct or augment an anatomy of the patient. The augmentation of the anatomy can include various procedures, such as movement or augmentation of bone, insertion of implantable devices, or other appropriate procedures. A surgeon can perform the procedure on the subject with images of the patient that can be acquired using imaging systems such as a magnetic resonance imaging (MRI) system, computed tomography (CT) system, fluoroscopy (e.g., C-Arm imaging systems), or other appropriate imaging systems.

Images of a patient can assist a surgeon in performing a procedure including planning the procedure and performing the procedure. A surgeon may select a two dimensional image or a three dimensional image representation of the patient. The images can assist the surgeon in performing a procedure with a less invasive technique by allowing the surgeon to view the anatomy of the patient without removing the overlying tissue (including dermal and muscular tissue) when performing a procedure.

SUMMARY

This section provides a general summary of the disclosure, and is not a comprehensive disclosure of its full scope or all of its features.

In some embodiments, the present disclosure provides an imaging system that can include an imaging capturing portion, an image processing unit, a main power supply and a supplemental power supply. The image capturing portion can include a source that emits an emission signal towards a target to be imaged, and a receiver that receives the emission signal emitted by the source. The image processing unit can receive the received emission signal from the imaging capturing portion and generate image data based on the received emission signal. The main power supply can be coupled to the imaging capturing portion and the imaging processing unit for providing operational power thereto. The supplemental power supply can be coupled to the main power supply and the imaging processing unit. The supplemental power supply can be charged by the main power supply in a first mode and provide operational power to the imaging processing unit in a second mode.

In further embodiments, the present disclosure provides a method of performing a procedure. The method can include the step of providing an imaging system that includes an image capturing portion, an image processing unit, a main power supply and a supplementary power supply. The image capturing portion can generate an emission signal that is received by the image processing unit, and the image processing unit can generate image data based on the received emission signal. The method can further include determining an operating mode of the imaging system to be a first mode or a second mode. In the first mode, the method can include providing operational power to the imaging processing unit from the main power supply and charging the supplementary power supply from the main power supply. In the second mode, the method can include providing operational power to the imaging processing unit from the supplemental power supply.

The present disclosure further provides, in some embodiments, a navigation system that can include a tracking system, an image capturing portion, an image processing unit, a main power supply, a supplemental power supply, and a display device. The tracking system can track an instrument relative to a target within a navigation space. The imaging capturing portion can include a source that emits an emission signal towards the target to be imaged, and a receiver that receives the emission signal emitted by the source. The image processing unit can receive the received emission signal from the imaging capturing portion and generate image data based on the received emission signal. The main power supply can be coupled to the imaging capturing portion and the imaging processing unit for providing operational power thereto. The supplemental power supply can be coupled to the main power supply and the imaging processing unit. The supplemental power supply can be charged by the main power supply in a first mode and provide operational power to the imaging processing unit in a second mode. The display device can display the image data and an icon representing the tracked instrument.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
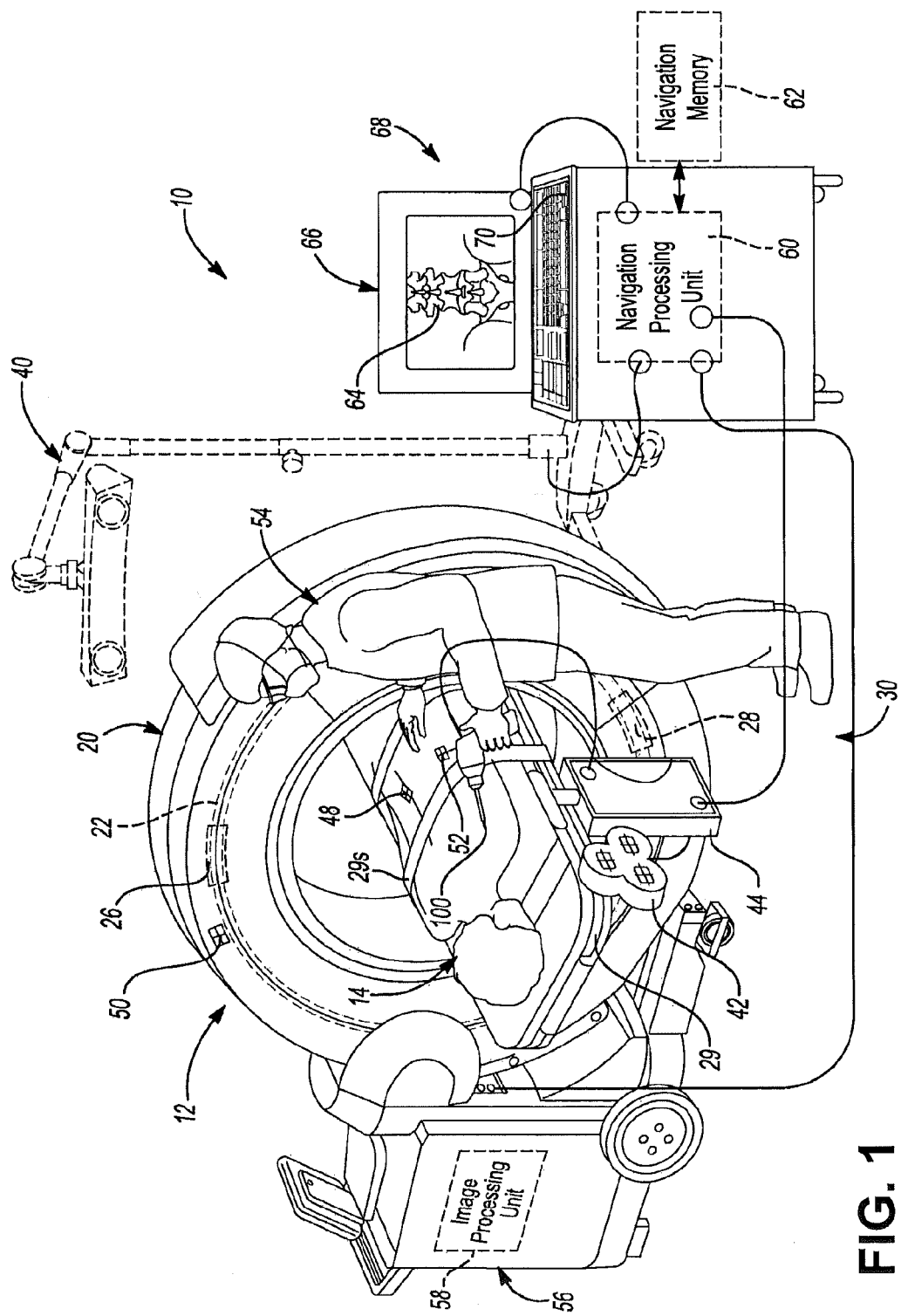
FIG. 1 is an environmental view of an operating theatre including an imaging system and a navigation system.

The following description is merely exemplary in nature. It should be understood that throughout the drawings, corresponding reference numerals indicate like or corresponding parts and features. As indicated above, the present teachings are directed toward an image-based navigation system, such as an O-Arm® imaging system sold by Medtronic Navigation, Inc. having a place of business in Louisville, Colo., USA. It should be noted, however, that the present teachings could be applicable to any appropriate imaging device, such as a C-arm imaging device. Further, as used herein, the term "module" can refer to a computer readable media that can be accessed by a computing device, an application specific integrated circuit (ASIC), an electronic circuit, a processor (shared, dedicated, or group) and memory that executes one or more software or firmware programs, a combinational logic circuit, and/or other suitable software, firmware programs or components that provide the described functionality.

FIG. 1 is a diagram illustrating an overview of a navigation system 10 that can be used for various procedures. The navigation system 10 can be used to track the location of an item, such as an implant or an instrument (100), relative to a subject, such as a patient 14. It should further be noted that the navigation system 10 may be used to navigate any type of instrument, implant, or delivery system, including: guide wires, arthroscopic systems, orthopedic implants, spinal implants, deep brain stimulation (DBS) probes, etc. Non-human or surgical procedures may also use the instrument 100 and the navigation system 10. Moreover, the instruments may be used to navigate or map any region of the body. The navigation system 10 and the various tracked items may be used in any appropriate procedure, such as one that is generally minimally invasive or an open procedure.

The navigation system 10 can interface with or integrally include an imaging system 12 that is used to acquire pre-operative, intra-operative, or post-operative, or real-time image data of the patient 14. It will be understood, however, that any appropriate subject can be imaged and any appropriate procedure may be performed relative to the subject. In the example shown, the imaging system 12 comprises an O-arm® imaging device sold by Medtronic Navigation, Inc. having a place of business in Louisville, Colo., USA. The imaging device 12 includes imaging portions such as a generally annular gantry housing 20 that encloses an image capturing portion 22. The image capturing portion 22 may include an x-ray source or emission portion 26 and an x-ray receiving or image receiving portion 28. The emission portion 26 and the image receiving portion 28 are generally spaced about 180 degrees from each other and mounted on a rotor (not illustrated) relative to a track of the image capturing portion 22. The image capturing portion 22 can be operable to rotate 360 degrees during image acquisition. The image capturing portion 22 may rotate around a central point or axis, allowing image data of the patient 14 to be acquired from multiple directions or in multiple planes.

The imaging system 12 can include those disclosed in U.S. Pat. Nos. 7,188,998; 7,108,421; 7,106,825; 7,001,045; and 6,940,941; all of which are incorporated herein by reference in their entirety. The imaging system 12 can also include or be associated with various image processing systems, as discussed herein. Other possible imaging systems can include C-arm fluoroscopic imaging systems which can also be used to generate three-dimensional views of the patient 14. It is also understood that other appropriate imaging systems can be used such as magnetic resonance imaging (MRI), positron emission tomography imaging (PET), etc.

The patient 14 can optionally be fixed onto an operating table 29. The table 29 can include a plurality of straps 29s. The straps 29s can be secured around the patient 14 to fix the patient 14 relative to the table 29. Various apparatuses may be used to position the patient 14 in a static position on the operating table 29. Examples of such patient positioning devices are set forth in commonly assigned U.S. patent application Ser. No. 10/405,068, published as U.S. Pat. App. Pub. No. 2004-0199072 on Oct. 7, 2004, entitled "An Integrated Electromagnetic Navigation And Patient Positioning Device", filed Apr. 1, 2003 which is hereby incorporated by reference. Other known apparatuses may include a Mayfield® clamp.

The navigation system 10 includes a tracking system 30 that can be used to track instruments relative to the patient 14 or within a navigation space. The navigation system 10 can use image data from the imaging system 12 and information from the tracking system 30 to illustrate locations of the tracked instruments, as discussed herein. The tracking system 30 can include a plurality of types of tracking systems including an optical tracking system that includes an optical localizer 40 and/or an electromagnetic (EM) tracking system that can include an EM localizer 42 that communicates with or through an EM controller 44. The optical tracking system 40 and the EM tracking system with the EM localizer 42 can be used together to track multiple instruments or used together to redundantly track the same instrument. Various tracking devices, including those discussed further herein, can be tracked with the tracking system 30 and the information can be used by the navigation system 10 to allow for an output system to output, such as a display device to display, a position of an item. Briefly, tracking devices, such as a patient tracking device or dynamic reference frame (to track the patient 14) 48, an imaging device tracking device 50 (to track the imaging device 12), and an instrument tracking device 52 (to track the instrument 100), allow selected portions of the operating theater to be tracked relative to one another with the appropriate tracking system, including the optical localizer 40 and/or the EM localizer 42.

It will be understood that any of the tracking devices 48-52 can be optical or EM tracking devices, or both, depending upon the tracking localizer used to track the respective tracking devices. It will be further understood that any appropriate tracking system can be used with the navigation system 10. Alternative tracking systems can include radar tracking systems, acoustic tracking systems, ultrasound tracking systems, and the like.

An exemplarily EM tracking system can include the STEALTHSTATION® AXIEM™ Navigation System, sold by Medtronic Navigation, Inc. having a place of business in Louisville, Colo. Exemplary tracking systems are also disclosed in U.S. Pat. No. 7,751,865, issued Jul. 6, 2010 and entitled "METHOD AND APPARATUS FOR SURGICAL NAVIGATION"; U.S. Pat. No. 5,913,820, titled "Position Location System," issued Jun. 22, 1999 and U.S. Pat. No. 5,592,939, titled "Method and System for Navigating a Catheter Probe," issued Jan. 14, 1997, all herein incorporated by reference in their entirety.

Further, for EM tracking systems it may be necessary to provide shielding or distortion compensation systems to shield or compensate for distortions in the EM field generated by the EM localizer 42. Exemplary shielding systems include those in U.S. Pat. No. 7,797,032, issued on Sep. 14, 2010 and U.S. Pat. No. 6,747,539, issued on Jun. 8, 2004; distortion compensation systems can include those disclosed in U.S. patent Ser. No. 10/649,214, filed on Jan. 9, 2004, published as U.S. Pat. App. Pub. No. 2004/0116803, all of which are incorporated herein by reference in their entirety.

With an EM tracking system, the localizer 42 and the various tracking devices can communicate through the EM controller 44. The EM controller 44 can include various amplifiers, filters, electrical isolation, and other systems. The EM controller 44 can also control the coils of the localizer 42 to either emit or receive an EM field for tracking. A wireless communications channel, however, such as that disclosed in U.S. Pat. No. 6,474,341, entitled "Surgical Communication Power System," issued Nov. 5, 2002, herein incorporated by reference in its entirety, can be used as opposed to being coupled directly to the EM controller 44.

It will be understood that the tracking system may also be or include any appropriate tracking system, including a STEALTHSTATION® TRIM®, TREON®, and/or S7™ Navigation System having an optical localizer, similar to the optical localizer 40, sold by Medtronic Navigation, Inc. having a place of business in Louisville, Colo. Further alternative tracking systems are disclosed in U.S. Pat. No. 5,983,126, to Wittkampf et al. titled "Catheter Location System and Method," issued Nov. 9, 1999, which is hereby incorporated by reference in its entirety. Other tracking systems include an acoustic, radiation, and radar tracking or navigation systems.

The imaging system 12 can further include a support housing or cart 56 that can house a separate image processing unit 58. The cart can be connected to the gantry 20. The navigation system 10 can include a navigation processing unit 60 that can communicate or include a navigation memory 62. The navigation processing unit 60 can include a processor, e.g., a computer processor, that executes instructions to determine locations of the tracking devices 48-52 based on signals from the tracking devices. The navigation processing unit 60 can receive information, including image data, from the imaging system 12 and tracking information from the tracking systems 30, including the respective tracking devices 48-52 and the localizers 40-42. Image data can be displayed as an image 64 on a display device 66 of a workstation or other computer system 68 (laptop, desktop, tablet computer, etc.), which may have a central processor to act as the navigation processing unit 60 by executing instructions. The workstation 68 can include appropriate input devices, such as a keyboard 70. It will be understood that other appropriate input devices can be included, such as a mouse, a foot pedal or the like which can be used separately or in combination. Also, all of the disclosed processing units or systems can be combined in a single processor (such as, a single central processing chip) that can execute different instructions to perform different tasks.

The image processing unit 58 generates image data based on information (the received emission signal) from the imaging system 12 and transmits it to the navigation processor 60. It will be further understood, however, that the imaging system 12 need not perform any image processing and it can transmit the information received from the imaging system 12 directly to the navigation processing unit 60. Accordingly, the navigation system 10 may include or operate with a single or multiple processing centers or units that can access single or multiple memory systems based upon system design.

In various embodiments, the imaging system 12 can generate image data that can be registered to the patient space or navigation space. In various embodiments, the position of the patient 14 relative to the imaging system 12 can be determined by the navigation system 10 with the patient tracking device 48 and the imaging system tracking device 50 to assist in registration. Accordingly, the position of the patient 14 relative to the imaging system 12 can be determined.

Alternatively, or in addition to tracking the imaging system 12, the imaging system 12, such as the O-arm® imaging system, can know its position and be repositioned to the same position within about 10 microns. This allows for a substantially precise placement of the imaging system 12 and precise determination of the position of the imaging device 12. Precise positioning of the imaging portion 22 is further described in U.S. Pat. Nos. 7,188,998; 7,108,421; 7,106,825; 7,001,045; and 6,940,941; all of which are incorporated herein by reference in their entirety.

Subject or patient space and image space can be registered by identifying matching points or fiducial points in the patient space and related or identical points in the image space. When the position of the imaging device 12 is known, either through tracking or its "known" position, or both, the image data is generated at a precise and known position. This can allow image data that is automatically or "inherently registered" to the patient 14 upon acquisition of the image data. Essentially, the position of the patient 14 is known precisely relative to the imaging system 12 due to the accurate positioning of the imaging system 12. This allows points in the image data to be known relative to points of the patient 14 because of the known precise location of the imaging system 12.

Alternatively, manual or automatic registration can occur by matching fiducial points in image data with fiducial points on the patient 14. Registration of image space to patient space allows for the generation of a translation map between the patient space and the image space. According to various embodiments, registration can occur by determining points that are substantially identical in the image space and the patient space. The identical points can include anatomical fiducial points or implanted fiducial points. Exemplary registration techniques are disclosed in U.S. Patent Application Publication No. 2010/0228117, filed on Mar. 9, 2009 incorporated herein by reference in its entirety.

Once registered, the navigation system 10 with or including the imaging system 12, can be used to perform selected procedures. Selected procedures can use the image data generated by or acquired with the imaging system 12. Further, the imaging system 12 can be used to acquire image data at different times relative to a procedure. As discussed herein, image data can be acquired of the patient 14 subsequent to a selected portion of a procedure for various purposes, including confirmation of the portion of the procedure.

With continuing reference to FIG. 1, the imaging system 12 can generate actual three dimensional images of the patient 14 or virtual three dimensional images based on the image data, which can be registered to the patient/navigation space. The patient 14 can be placed relative to the imaging system 12 to allow the imaging system 12 to obtain image data of the patient 14. To generate 3D image data, the image data can be acquired from a plurality of views or positions relative to the patient 14. The 3D image data of the patient 14 can be used alone or with other information to assist in performing a procedure on the patient 14 or an appropriate subject. It will be understood, however, that any appropriate imaging system can be used, including magnetic resonance imaging, computed tomography, fluoroscopy, etc.

As generally illustrated in FIG. 1, the navigation system 10 can be used to navigate the instrument 100 relative to the patient 14. The navigation can be imageless (only illustrating icons at tracked locations of different tracked portions) or with images. Images can include acquired images (such as, from the imaging system 12 or atlas images). Regardless, icons with or without images can be displayed on the display device 66. The tracking system 30 can track the instrument 100 and the navigation processing unit 60 can be used to determine the location of the instrument 100 and display the location of the instrument on the display 66 relative to the image 64 or, as mentioned above, without the image 64. Accordingly, according to various embodiments, such as those discussed herein, the user 54 (such as, a surgeon) can view an icon representing a location of the instrument 100 relative to the patient 14 or a selected portion of the patient 14 with or without images on the display 66. In so viewing the icons, the user 54 can know the location of the instrument 100 in subject/patient space based upon the tracked location of the instrument 100 in image space.

Figure 2:
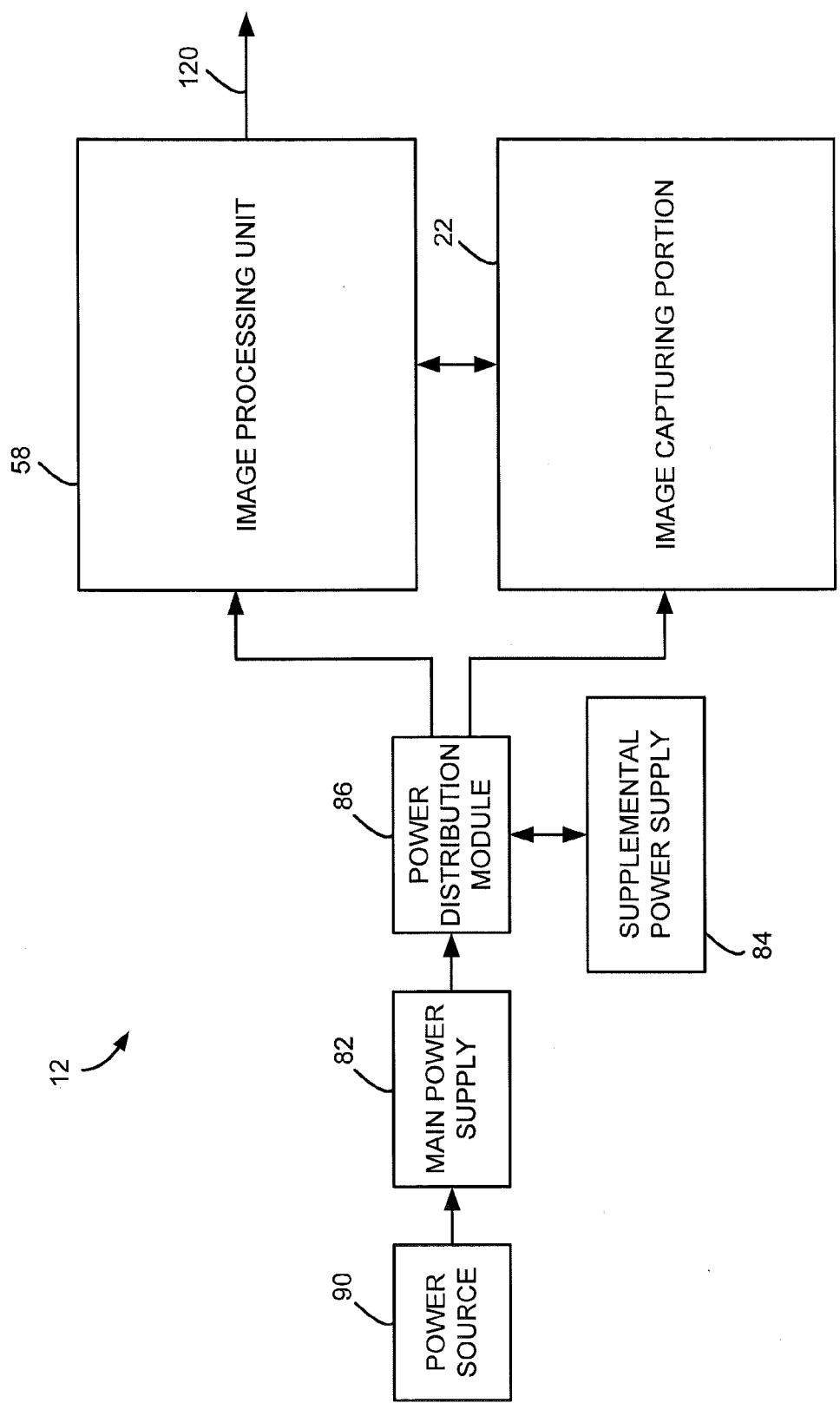
FIG. 2 is a block diagram of an example imaging system according to some embodiments of the present disclosure.

Referring now to FIG. 2, a block diagram of an example imaging system 12 according to some embodiments of the present disclosure is illustrated. The imaging system 12 can include the image processing unit 58, the image capturing portion 22, a main power supply 82 and a supplemental power supply 84. The imaging system 12 can receive its operational power from a power source 90. In some embodiments, the power source 90 is a standard 110V/15 Ampere outlet to which the imaging system 12 can be coupled, e.g., by a plug (not shown). The power source 90 can be coupled to the main power supply 82, the supplemental power supply 84, and a power distribution module 86, as described below. The main power supply 82 can include, for example, an AC/DC converter and signal filtering/conditioning circuit(s) for providing the appropriate DC voltage to the imaging system 12 and its components.

The image capturing portion 22 can include a source (such as, an X-ray source 26) and a receiver (such as, an X-ray receiver 28). During imaging, the source (X-ray source 26) emits an emission signal towards a target, e.g., patient 14, to be imaged. The emission signal travels through the target and is received by the receiver (X-ray receiver 28). The emission signal received by the receiver 28 can be utilized by the imaging system 12 to generate image data 120 of the target. The image data 120 can, for example, be output to the navigation processing unit 60 and/or displayed on the display device 66 as an image 64, which can be utilized by the user 54 to assist with the procedure being performed, as is described above.

In order to generate the image data 120 from the received emission signal, the image processing unit 58 can include relatively high-performance computing devices, such as one or more high-performance processors, graphics cards, etc. These high-performance computing devices can require a large amount of power to operate (operational power). For example only, the high-performance computing devices can require 1000 or more watts. In some cases, the power available from the power source 90 can be insufficient to meet the power needs of such high-performance computing devices. Thus, main power supply 82, which receives its operational power from the power source 90, may be unable to provide operational power to the image processing unit 58 during high-performance operation.

In order to provide additional power, the imaging system 12 can include a supplemental power supply 84. The supplemental power supply 84 can comprise, for example, a rechargeable battery array, a plurality of capacitors or other power storage media. For example only, the rechargeable battery array can include a plurality of Lead Acid or Lithium-ion batteries, each battery providing twelve volts with a capacity of nine to fifteen ampere hours. In some embodiments, the supplemental power supply 84 can receive power or be charged from the main power supply 82 during "normal" (or low powered) operation of the imaging system 12, which is then stored at the supplemental power supply 84. This stored power can then be utilized and drawn upon by the imaging system 12 during periods of high-powered operation, such as during generation of the image data by the image processing unit 58.

In a first mode of operation, the imaging system 12 can receive its operational power from the main power supply 82. The first mode of operation can be, for example, during "normal" operation of the imaging system 12, such as when manipulating already generated image data, displaying tracked instrument(s) 100 on the image 64 shown on the display device 66, etc. In a second mode of operation, however, the imaging system 12 can receive its operational power from the supplementary power supply 84 or from the supplementary power supply 84 as well as the main power supply 82. The second mode of operation can be, for example, during high-powered operation of the imaging system 12, such as generating image data from the received emission signal(s), performing algebraic reconstruction of the image data, etc.

In some embodiments, the power distribution module 86 can determine whether to operate the imaging system 12 in the first mode or second mode of operation. The power distribution module 86 can, for example, determine the operating mode of the imaging system 12 by monitoring a power draw of the imaging system 12 from the main power supply 82 and comparing the drawn power to a threshold. The threshold can be set, for example, to a level just below but approximately equal to (−5-10%) the maximum power available from the main power supply 82 and/or power source 90. If the power drawn by the imaging system is below the threshold, the power distribution module 86 can determine that the first mode of operation is acceptable and provide operational power to the imaging system 12 from the main power supply 82. In the event that the power drawn by the imaging system is equal to or above the threshold, the power distribution module 86 can determine that the second mode of operation is desired and provide operational power to the imaging system 12 from the supplemental power supply 84 or from the supplementary power supply 84 as well as the main power supply 82.

In various embodiments of the present disclosure, during the first mode of operation, i.e., operation of the imaging system 12 from the main power supply 82, the supplemental power supply 84 can be charged from the main power supply 82 such that the supplemental power supply 84 is prepared to provide operational power to the imaging system 12 during second mode operation. The power distribution module 86, for example, can control the distribution of power from the main power supply 82 to the image processing unit 58, the image capturing portion 22, and/or supplemental power supply 84 as is desired.

Figure 3:
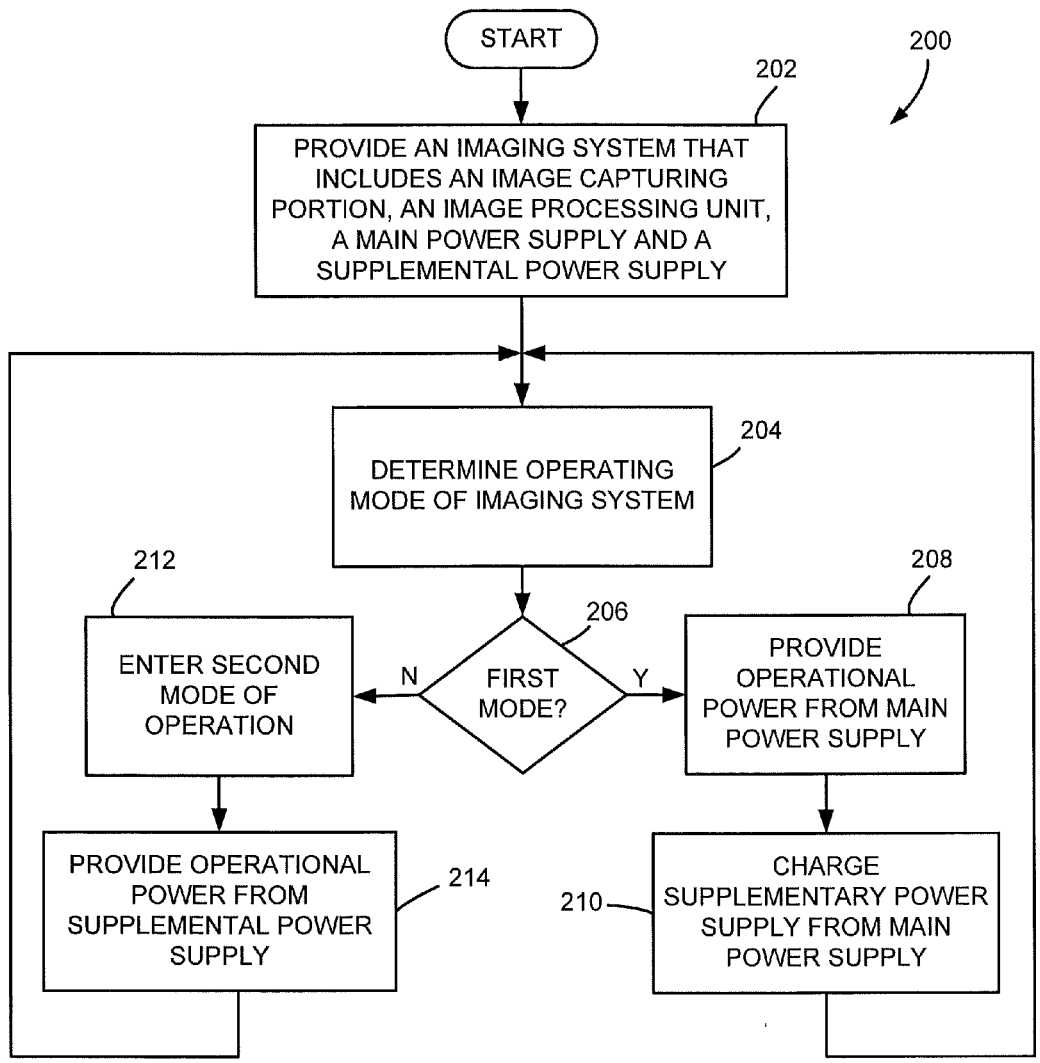
FIG. 3 is a flow chart of an example method of performing a procedure according to some embodiments of the present disclosure.

Referring now to FIG. 3, a flow chart of an example method 200 of performing a procedure is illustrated. The method 200 includes the step of providing an imaging system 12 at step 202. The imaging system 12 can include an image capturing portion 22, an image processing unit 58, a main power supply 82 and a supplemental power supply 84, as described above. At step 204, the operating mode of the imaging system 12 is determined. If the determined operating mode is a first mode at step 206, the method 200 proceeds to step 208 at which operational power is provided to the imaging system 12 from the main power supply 82. At step 210, the supplementary power supply 84 is charged from the main power supply 82, after which the method 200 returns to step 204. If the determined operating mode is a second mode at step 206, the method 200 proceeds to step 212 at which the imaging system 12 enters the second mode of operation. At step 214, operational power is provided to the imaging system 12 from the supplementary power supply 82 (alone or in conjunction with main power supply 82), after which the method 200 returns to step 204. For example only, the operational power may be provided to the imaging system 12 from the supplementary power supply 82 (alone or in conjunction with main power supply 82) for a period of time sufficient to complete high-power operation, such as algebraic reconstruction, e.g., between 2-3 minutes.

Figure 4:
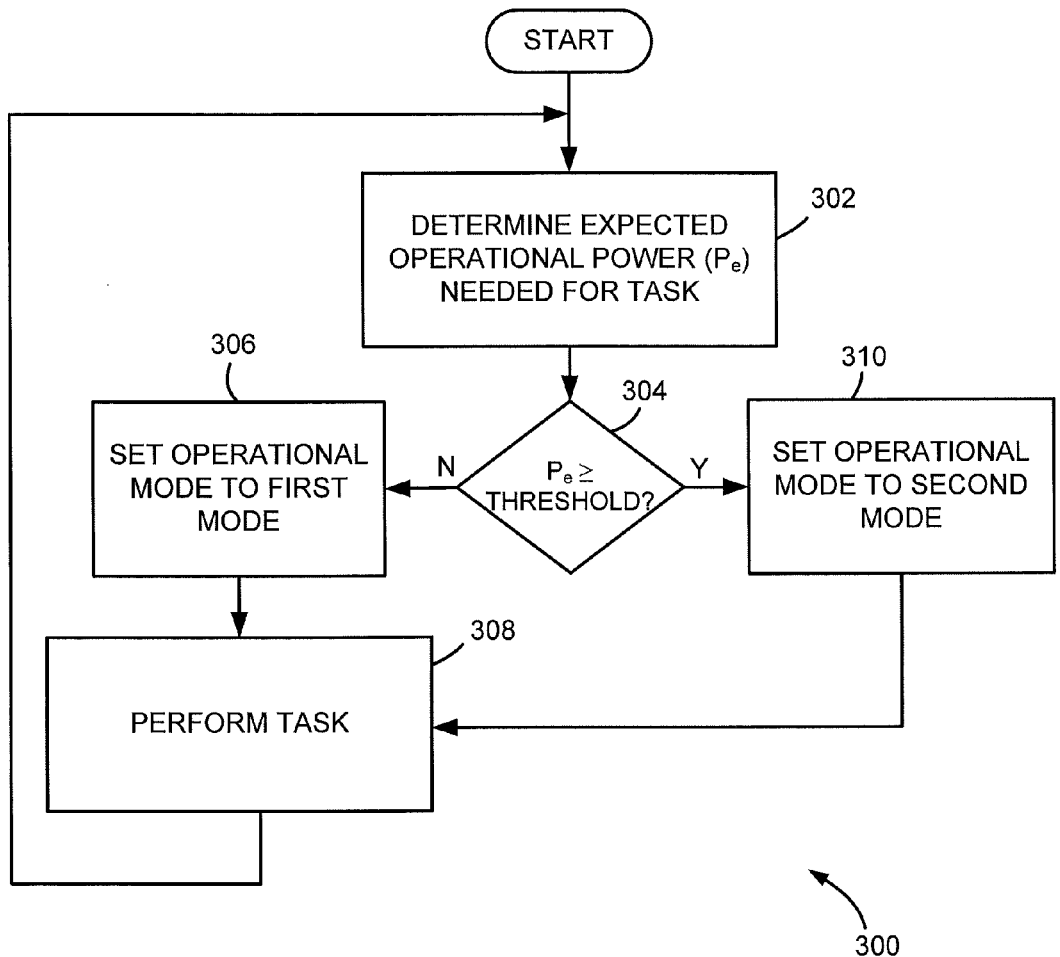
FIG. 4 is a flow chart of an example method of determining an operating mode of an imaging system according to some embodiments of the present disclosure.

Referring now to FIG. 4, a flow chart of an example method 300 of determining an operating mode of an imaging system 12 according to some embodiments of the present disclosure is illustrated. The method 300 can, for example, be performed by the power distribution module 86 and can take place at step 204 of the method 200 described above.

The method begins at step 302 at which the expected operational power ($P_e$) needed for performing a specific task of the imaging system 12 is determined. Examples of specific tasks include, but are not limited to, imaging a target (emitting and receiving an emission signal), generating image data based on the received emission signal, and performing algebraic reconstruction on the image data. At step 304, the expected operational power ($P_e$) is compared to a threshold. The threshold can be set, for example, to a level just below but approximately equal to (−5-10%) the maximum power available from the main power supply 82 and/or power source 90. If the expected operational power ($P_e$) is less than the threshold, the method 300 proceeds to step 306 at which the operational mode is set to the first mode. At step 308, the specific task is performed, after which the method 300 returns to step 302. If, instead, the expected operational power ($P_e$) is greater than or equal to the threshold, the method 300 proceeds to step 310 at which the operational mode is set to the second mode. The method 300 then proceeds to step 308 at which the specific task is performed, after which the method 300 returns to step 302.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. An imaging system comprising:
   a plurality of devices configured to capture an image of a patient, wherein the plurality of devices comprise
     (i) a source that emits an emission signal towards the patient, and
     (ii) a receiver that receives the emission signal emitted by the source and generates an image signal;
   an image processing unit that receives the image signal from the receiver and generates image data;
   a main power supply;
   a supplemental power supply; and
   a power distribution module configured to (i) receive power from the main power supply and the supplemental power supply, (ii) during a first mode, control distribution of power from the main power supply to the source, the image processing unit, and the supplemental power supply, and (iii) during a second mode, control distribution of power from the main power supply and the supplemental power supply to the image processing unit, wherein the power distribution module does not supply power from the supplemental power supply to the image processing unit during the first mode,
   wherein the power distribution module is configured to, during the first mode, charge the supplemental power supply by supplying power from the main power supply to the supplemental power supply.

2. The imaging system of claim 1, wherein the image processing unit is configured to generate the image data based on the received emission signal during the second mode.

3. The imaging system of claim 1, wherein the supplemental power supply comprises a rechargeable battery array.

4. The imaging system of claim 1, wherein the source comprises an X-ray source and the receiver comprises an X-ray receiver.

5. The imaging system of claim 1, wherein the power distribution module is configured to:
   monitor an amount of power drawn from the main power supply;
   compare the amount of power drawn to a threshold, wherein the threshold is less than a maximum amount of power available from the main power supply;
   if the power drawn is less than the threshold, operate in the first mode; and
   if the power drawn is greater than or equal to the threshold, operate in the second mode.

6. The imaging system of claim 1, wherein the power distribution module is configured to determine whether to operate in the first mode or the second mode by:
   determining an expected amount of operational power to be drawn from the power distribution module;
   comparing the expected amount of operational power to a threshold; and
   transitioning from the first mode to the second mode if the expected amount of operational power is greater than the threshold.

7. The imaging system of claim 1, wherein the image processing unit is configured to generate the image data by algebraic reconstruction.

8. The imaging system of claim 1, wherein the the power distribution module is configured to transition from the first mode to the second mode if an amount of power drawn from the power distribution module is greater than a threshold.

9. A method of operating an imaging system, wherein the imaging system comprises a source, a receiver, an image processing unit, a main power supply, a supplemental power supply, and a power distribution module, the method comprising:
   generating an emission signal via the source and directing the emission signal at a patient;
   receiving the emission signal via the receivier;
   generating an image signal based on the emission signal;
   receiving the image signal at the image processing unit;
   generating image data based on the image signal;
   determining whether to operate the imaging system in a first mode or a second mode;
   while operating in the first mode, controlling distribution of power from the main power supply to the source, the image processing unit, and the supplemental power supply;
   while operating in the first mode, charging the supplemental power supply by supplying power from the main power supply to the supplemental power supply; and
   while in the second mode, supplying power from the supplemental power supply to the imaging processing unit.

10. The method of claim 9, wherein determining whether to operate the imaging system in the first mode or the second mode comprises:
   determining an expected power needed for a task;
   comparing the expected power to a threshold;
   operating in the first mode if the expected power is less than the threshold; and
   operating in the second mode if the expected power is greater than or equal to the threshold.

11. The method of claim 9, wherein determining whether to operate the imaging system in the first mode or the second mode comprises:
- determining an amount of power drawn by the imaging system;
- comparing the amount of power to a threshold;
- operating in the first mode if the amount of power is less than the threshold; and
- operating in the second mode if the amount of power is greater than or equal to the threshold.

12. The method of claim 9, further comprising generating the image data based on the received emission signal during the second mode.

13. The method of claim 9, wherein the supplemental power supply comprises a battery array.

14. The method of claim 9, wherein:
- the source comprises an X-ray source; and
- the receiver comprises an X-ray detector.

15. The method of claim 9, comprising generating the image data via algebraic reconstruction.

16. A navigation system comprising:
- a tracking system for tracking an instrument relative to a target within a navigation space;
- the imaging system of claim 1; and
- a display device for displaying the image data and an icon representing the tracked instrument.

17. The navigation system of claim 16, wherein the navigation system tracks a location of the plurality of devices to assist in registering a position of the target.

18. The imaging system of claim 1, wherein:
- during the second mode, the image processing unit is configured to generate the image data; and
- during the first mode, the image processing unit is configured to (i) manipulate the image data, based on the manipulated image data, display an image on a display, and display a tracked instrument on the image.

19. The imaging system of claim 5, wherein the threshold is less than or equal to 90-95% of the maximum amount of power available from the main power supply.

* * * * *